United States Patent
Lynch

(10) Patent No.: US 11,931,153 B2
(45) Date of Patent: Mar. 19, 2024

(54) ELECTRONIC DEVICE, A WEARABLE ARTICLE INCORPORATING AN ELECTRONIC DEVICE AND A SYSTEM COMPRISING AN ELECTRONIC DEVICE AND A WEARABLE ARTICLE

(71) Applicant: Prevayl Innovations Limited, Manchester (GB)

(72) Inventor: Michael John Lynch, Cheshire (GB)

(73) Assignee: Prevayl Innovations Limited, Manchester (GB)

( * ) Notice: Subject to any disclaimer, the term of this patent is extended or adjusted under 35 U.S.C. 154(b) by 11 days.

(21) Appl. No.: 17/789,360

(22) PCT Filed: Jan. 19, 2021

(86) PCT No.: PCT/GB2021/050115
§ 371 (c)(1),
(2) Date: Jun. 27, 2022

(87) PCT Pub. No.: WO2021/148782
PCT Pub. Date: Jul. 29, 2021

(65) Prior Publication Data
US 2023/0121861 A1    Apr. 20, 2023

(30) Foreign Application Priority Data

Jan. 21, 2020   (GB) ..................... 2000855

(51) Int. Cl.
*A61B 5/26* (2021.01)
*A61B 5/053* (2021.01)
(Continued)

(52) U.S. Cl.
CPC .............. *A61B 5/256* (2021.01); *A61B 5/053* (2013.01); *A61B 5/30* (2021.01); *G06F 1/163* (2013.01)

(58) Field of Classification Search
CPC ........... A61B 5/256; A61B 5/30; A61B 5/053; G06F 1/163
See application file for complete search history.

(56) References Cited

U.S. PATENT DOCUMENTS

2014/0189928 A1 *   7/2014   Oleson ................. A61B 5/6804
                                                          600/388
2015/0119675 A1     4/2015   Kaneko
(Continued)

FOREIGN PATENT DOCUMENTS

FR    3077723    8/2019
GB    2555592    2/2019
(Continued)

OTHER PUBLICATIONS

International Search Report received in PCT/GB2021/050115 dated Apr. 13, 2021.
(Continued)

*Primary Examiner* — Adam Z Minchella
(74) *Attorney, Agent, or Firm* — Suzannah K. Sundby, Esq.; Canady + Lortz LLP

(57) ABSTRACT

A wearable article (1) includes a sensor assembly (104) for sensing biosignals of a wearer of the wearable article, and an electronic device (102) that can be attached to the sensor assembly to receive and the process biosignals. The electronic device is detachable from the garment and includes a housing (128a, 128b). The electronic device is retained in place by means of a magnet (132) within the housing which cooperates with a magnet on the garment. The sensor assembly includes a sensing electrodes and conductors (112; 122a) which couple the sensing electrodes to an interface that is configured to couple the sensed biosignals to the electronic device. The electronic device attaches to the garment at the interface. The electronic device includes one or more contacts (138b) which engage with the interface at (Continued)

the conductors so that biosignals can be coupled to the electronic device. The garment can also include a locating ring (130) to help locate the electronic device on the garment. The electronic device can be easily attached by a wearer, for example with the use of only one hand.

22 Claims, 9 Drawing Sheets

(51) Int. Cl.
*A61B 5/256* (2021.01)
*A61B 5/30* (2021.01)
*G06F 1/16* (2006.01)

(56) References Cited

U.S. PATENT DOCUMENTS

| | | |
|---|---|---|
| 2015/0342269 A1 | 12/2015 | Oleson |
| 2016/0128632 A1 | 5/2016 | Wiebe |
| 2016/0174840 A1* | 6/2016 | Udoh ..................... G16Z 99/00 600/595 |
| 2016/0270727 A1* | 9/2016 | Berg ..................... A61B 5/389 |
| 2016/0345850 A1 | 12/2016 | Brockway |
| 2017/0279230 A1* | 9/2017 | Komoto ............. H01R 13/2442 |
| 2018/0271414 A1 | 9/2018 | Deck |
| 2018/0317783 A1 | 11/2018 | Petrikovsky |
| 2019/0059756 A1 | 2/2019 | Rasmussen |
| 2021/0030297 A1* | 2/2021 | Kouider ................... A61B 5/31 |

FOREIGN PATENT DOCUMENTS

| | | |
|---|---|---|
| GB | 2588253 | 4/2021 |
| WO | 2012112934 | 8/2012 |

OTHER PUBLICATIONS

Written Opinion received in PCT/GB2021/050115 dated Apr. 13, 2021.
Ulbrich et al., The IMPACT shirt: textile integrated and portable impedance cardiography, Jun. 1, 2014, pp. 1181-1196, vol. 35, No. 6, Publisher: Physiol Meas.
Prosecution history of granted foreign patent GB2588253.

* cited by examiner

ELECTRONIC DEVICE, A WEARABLE ARTICLE INCORPORATING AN ELECTRONIC DEVICE AND A SYSTEM COMPRISING AN ELECTRONIC DEVICE AND A WEARABLE ARTICLE

CROSS REFERENCE TO RELATED APPLICATIONS

This application claims priority from United Kingdom Patent Application number 2000855.3 filed on 21 Jan. 2020, the whole contents of which are incorporated herein by reference.

BACKGROUND

The present invention is directed towards an electronic device and a wearable article incorporating an electronic device, particularly, although not exclusively, for sensing biosignals from a wearer of the wearable article. The present invention is also directed to a system comprising an electronic device and a wearable article.

Wearable articles, such as garments, incorporating sensors are wearable electronics used to measure and collect information from a wearer. Such wearable articles are commonly referred to as 'smart clothing'. It is advantageous to measure biosignals of the wearer during exercise.

It is known to provide a garment, or other wearable article, to which an electronic device (i.e. an electronic module, or related components) is attached in a prominent position, such as on the chest or between the shoulder blades.

Even if the electronic device is relatively comfortable to wear, attaching and removing the electronic device can be difficult to do quickly and easily, particularly without using two hands or without having to stop and manually arrange the garment so that the electronic device can be easily attached and detached.

SUMMARY

According to the present disclosure there is provided a biosensing garment and method as set forth in the appended claims. Other features of the invention will be apparent from the dependent claims, and the description which follows.

According to a first aspect of the present invention, there is provided an electronic device for a wearable article, the electronic device being configured to receive biosignals from a sensor assembly provided on the wearable article and including one or more sensing electrodes. The electronic device comprises: a housing arranged to house components configured to receive and process the received biosignals; and a signal coupling mechanism configured, when the electronic device is attached to the wearable article at an electronic device interface of the sensor assembly, to couple the biosignals to the components from the sensor assembly.

The signal coupling mechanism comprises at least one contact coupled to the components and configured to engage with the sensor assembly at a terminal of a respective sensing electrode.

The at least one contact is flexible and configured to flex between a first position and a second position in which the at least one contact engages with the terminal of the respective sensing electrode, wherein the at least one contact is flexed into the second position when the electronic device is attached to the wearable article.

Preferably, the components are mounted on a circuit board located within the housing and the at least one contact is connected to the components on the circuit board.

Preferably, the housing includes at least one aperture in the base of the housing and through which a portion of the at least one contact extends to engage with the terminal of the respective sensing electrode when in the second position.

Preferably, the portion of the at least one contact is a projection which engages the terminal of the respective sensing electrode.

Preferably, the at least one contact is L-shaped and includes an arm extending inwardly of the housing, and the projection is a V-shaped projection from the arm.

Preferably, the housing has a base arranged to contact the wearable article in use. The base may have a circular cross-section with a central axis along which the housing may rotate. i The housing may be a circular housing with a central axis around which the circular housing can rotate.

Preferably, the circular housing includes an outer wall, and a circumferential surface extending radially inwards from the outer wall and defining an internal circular recess, the circumferential surface being configured to maintain alignment of the at least one contact within the circular housing.

Preferably, the at least one aperture is located on a diameter of the circular housing.

More preferably, the at least one aperture is located coincidentally with the central axis.

Preferably, the circular housing includes two or more apertures in the base of the housing, each of the apertures being located on an internal diameter of the circular housing, and the electronic device has two or more electrodes, and wherein a portion of each contact extends through a respective one of the two or more apertures to engage with a terminal of the respective sensing electrode.

Preferably, one of the two or more apertures is located coincidentally with the central axis, and another of the two or more apertures is displaced radially from the one of the two or more apertures.

Preferably, the circular housing includes three apertures in the base of the housing each of the three apertures being located on an internal diameter of the circular housing, a first of these three apertures being located centrally on the base of the housing and coincident with the central axis of the circular housing, and second and third apertures being located equidistantly of the first aperture and on the diameter of the circular housing, and the electronic device has three contacts, and wherein a portion of each contact extends through a respective one of the three apertures to engage with the terminal of the respective sensing electrode, and wherein a first contact is configured to cooperate with the centrally located aperture whilst second and third contacts are configured to cooperate with respective second and third apertures, and wherein the second and third contacts are coupled to each other.

Preferably, the housing may include a keying mechanism configured to engage with a keying mechanism on the garment.

According to a second aspect of the present invention, there is provided a wearable article including a sensor assembly for sensing biosignals of a wearer of the wearable article. The sensor assembly comprises at least one sensing electrode for sensing the biosignals; and an electronic device interface coupled to the at least one sensing electrodes and configured to couple the sensed biosignals to an electronic device. Each of the at least one sensing electrodes includes a terminal configured to engage with a signal coupling mechanism of the electronic device, when the electronic device is attached to the sensor assembly at the electronic device interface, such that the biosignals are coupled from the sensor assembly to the electronic device.

Preferably, the terminal of each of the at least one sensing electrodes includes a terminating portion, the terminating portion having a configuration that defines the electronic device interface.

Preferably, the terminating portion has an arc-shaped configuration.

Alternatively, the terminating portion has a circular configuration. Alternatively, the terminating portion has a disk-shaped configuration.

Preferably, the sensor assembly comprises two or more sensing electrodes, each sensing electrode including a terminating portion of substantially circular configuration, with different radii and being concentrically arranged.

Preferably, the sensor assembly comprises two or more sensing electrodes, each sensing electrode including a terminating portion, and wherein the terminating portion of an inner one of the two or more sensing electrodes is located coincidentally with a central axis, and the terminating portions of the other outer one or more sensing electrodes has an arced configuration arranged around the inner one of the two or more sensing electrodes and around the central axis.

Preferably, the sensor assembly comprises two or more sensing electrodes, each sensing electrode including a terminating portion, and wherein the terminating portion of an inner one of the two or more sensing electrodes is located coincidentally with a central axis, and the terminating portions of the other outer one or more sensing electrodes has a circular configuration arranged concentrically around the inner one of the two or more sensing electrodes.

Preferably, the outer terminating portion has piecewise configuration with gaps formed therein.

Preferably, the sensing electrodes are located on a first surface of the wearable article and the electronic device interface is located on a second surface of the wearable article.

According to a third aspect of the present invention, there is provided an electronic device for a wearable article, the electronic device being configured to receive biosignals from a sensor assembly provided on the wearable article, the electronic device comprising: a housing arranged to house components configured to receive and process the received biosignals; and an attachment mechanism to releasably attach the housing to the wearable article.

Preferably, the attachment mechanism comprises a magnet mounted within the housing and arranged to cooperate with a respective magnet provided on the wearable article.

Preferably, the magnet is mounted within the housing towards a base of the housing.

Preferably, housing is a circular housing having a central axis and the magnet is a circular magnet retained within the circular housing, the circular magnet having an axis coincident with the central axis and arranged for rotational.

Preferably, the circular housing includes an internal outer wall and a circumferential surface extending radially from the internal wall and defining a circular internal recess configured to maintain alignment of the magnet within the housing.

Preferably, the electronic device may comprise some or all of the features of the electronic device of the first aspect of the disclosure.

According to a fourth aspect of the present invention, there is provided a wearable article including a sensor assembly for sensing biosignals of a wearer of the wearable article, the sensor assembly comprising at least one sensing electrode for sensing the biosignals and having an electronic device interface coupled to the at least one sensing electrode and configured to couple the sensed biosignals to an electronic device, the sensor assembly further including a sensor assembly attachment mechanism for releasably attaching the electronic device to the wearable article at the electronic device interface.

Preferably, the sensor assembly attachment mechanism comprises a magnet provided on a first surface of the wearable article and arranged to cooperate with a magnet mounted within the electronic device to releasably attach the electronic device to the electronic device interface.

Preferably, the magnet is aligned with the electronic device interface. Preferably, the magnet is a circular magnet.

Preferably, the sensor assembly is provided on a second surface of the wearable article, the second surface being arranged to be located away from the wearer's skin and the first surface being arranged to be located towards the wearer's skin.

Preferably, the wearable article may comprise some or all of the features of the wearable article of the second aspect of the disclosure.

In yet another aspect of the present invention, there is provided a wearable article including a sensor assembly for sensing biosignals of a wearer of the wearable article, the sensor assembly comprising at least one sensing electrode for sensing the biosignals and having an electronic device interface coupled to the at least one sensing electrode and configured to couple the sensed biosignals to an electronic device. The sensor assembly further includes a locating element configured to locate the electronic device against the electronic device interface.

Preferably, the locating element is arranged to circumscribe the electronic device interface.

Preferably, the locating element is a circular ring.

Preferably, the locating element is arranged to enclose a terminating portion of the electronic device interface.

Preferably, the locating element is arranged to receive a portion of the electronic device therein.

Preferably, the locating element has a cross-sectional profile that matches the profile of the electronic device to provide a frictional fit for the electronic device when located within the locating element.

Preferably, the locating element is formed of a resilient material.

Preferably, the locating element is a keying mechanism.

Preferably, the locating element may include a keying mechanism.

Preferably, the locating element is located on the outer surface of the wearable article.

Preferably, the wearable article may comprise some or all of the features of the wearable article of the second or fourth aspect of the disclosure.

According to yet another aspect of the present invention, there is provided a biosignal measuring system comprising a wearable article and an electronic device configured for attachment to the wearable article and configured to receive biosignals from the wearable article. The wearable article includes a sensor assembly for sensing biosignals of a wearer of the wearable article, the sensor assembly comprising: at least one sensing electrode for sensing the biosignals; and an electronic device interface coupled to the at least one sensing electrodes and configured to couple the sensed biosignals to the electronic device, each of the at least one sensing electrodes including a terminal configured to engage with a signal coupling mechanism of the electronic device, when the electronic device is attached to the sensor assembly at the electronic device interface, such that the biosignals are coupled from the sensor assembly to the electronic device.

Preferably, the electronic device includes one or more sensing electrodes, the electronic device comprising: a housing arranged to house components configured to receive and process the received biosignals; and a signal coupling mechanism configured, when the electronic device is attached to the wearable article at an electronic device interface of the sensor assembly, to couple the biosignals to the components from the sensor assembly.

According to yet another aspect of the present invention, there is provided a biosignal measuring system comprising a wearable article and an electronic device configured for attachment to the wearable article and configured to receive biosignals from the wearable article, wherein the wearable article includes a sensor assembly for sensing biosignals of a wearer of the wearable article, the sensor assembly comprising at least one sensing electrode for sensing the biosignals and having an electronic device interface coupled to the at least one sensing electrode and configured to couple the sensed biosignals to the electronic device, the sensor assembly further including a sensor assembly attachment mechanism for releasably attaching the electronic device to the wearable article at the electronic device interface.

Preferably, the electronic device includes a housing arranged to house components configured to receive and process the received biosignals; and an attachment mechanism configured to cooperate with the sensor assembly attachment mechanism to releasably attach the housing to the wearable article.

According to yet another aspect of the invention, there is provided a biosignal measuring system comprising a wearable article and an electronic device configured for attachment to the wearable article and configured to receive biosignals from the wearable article, wherein the wearable article includes a sensor assembly for sensing biosignals of a wearer of the wearable article, the sensor assembly comprising at least one sensing electrode for sensing the biosignals and having an electronic device interface coupled to the at least one sensing electrode and configured to couple the sensed biosignals to the electronic device, the sensor assembly further including a locating element configured to locate the electronic device against the electronic device interface.

In a wearable article of the present invention, manufacture of the wearable article may be simplified. In addition, it may be easier to clean a wearable article which has fewer electronic components attached thereto or incorporated therein. Furthermore, as the electronic device is removable, it may be easier to maintain and/or troubleshoot than embedded electronics.

BRIEF DESCRIPTION OF THE DRAWINGS

Examples of the present disclosure will now be described with reference to the accompanying drawings, in which.

DETAILED DESCRIPTION

Figure 1:
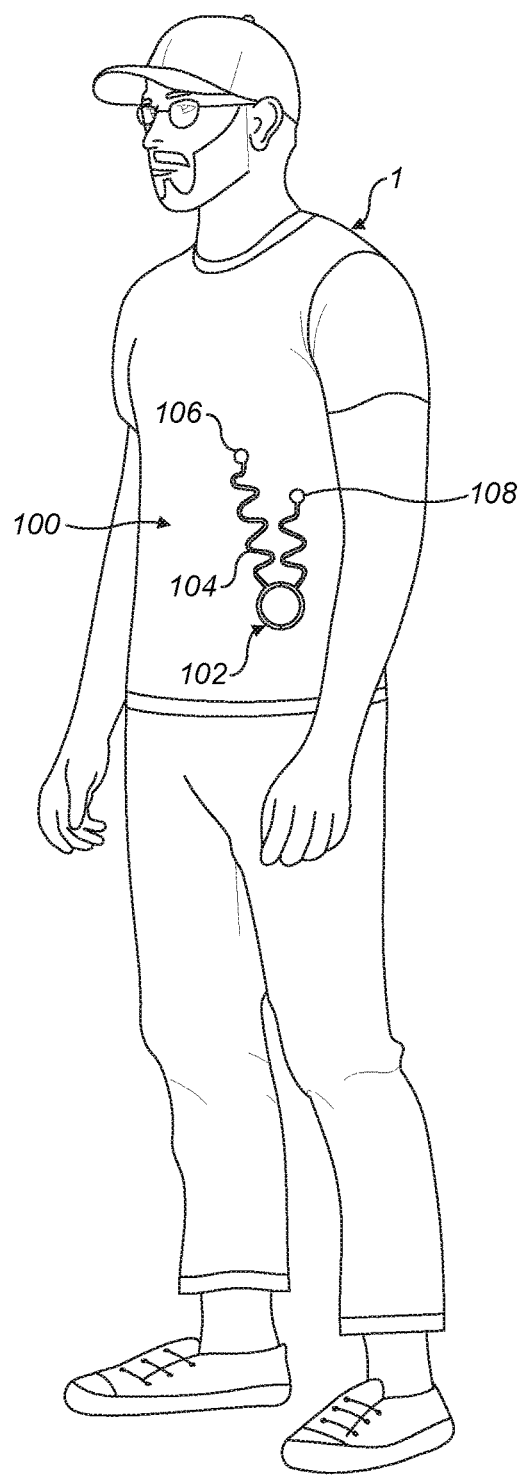
FIG. 1 shows a schematic illustration of a person wearing a wearable article of the invention.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

"Wearable article" as referred to throughout the present disclosure may refer to any form of electronic device which may be worn by a user such as a smart watch, necklace, garment, bracelet, or glasses. The wearable article may be a textile article. The wearable article may be a garment. The garment may refer to an item of clothing or apparel. The garment may be a top. The top may be a shirt, t-shirt, blouse, sweater, jacket/coat, or vest. The garment may be a dress, garment brassiere, shorts, pants, arm or leg sleeve, vest, jacket/coat, glove, armband, underwear, headband, hat/cap, collar, wristband, stocking, sock, or shoe, athletic clothing, swimwear, wetsuit or dry suit.

The wearable article/garment may be constructed from a woven or a non-woven material. The wearable article/ garment may be constructed from natural fibres, synthetic fibres, or a natural fibre blended with one or more other materials which can be natural or synthetic. The yarn may be cotton. The cotton may be blended with polyester and/or viscose and/or polyamide according to the application. Silk may also be used as the natural fibre. Cellulose, wool, hemp and jute are also natural fibres that may be used in the wearable article/garment. Polyester, polycotton, nylon and viscose are synthetic fibres that may be used in the wearable article/garment.

The garment may be a tight-fitting garment. Beneficially, a tight-fitting garment helps ensure that the sensor devices of the garment are held in contact with or in the proximity of a skin surface of the wearer. The garment may be a compression garment. The garment may be an athletic garment such as an elastomeric athletic garment.

In the embodiment described herein, a garment 1 is for use in measuring biosignals of a wearer.

"Biosignal" as referred to throughout the present disclosure may refer to signals from living beings that can be continually measured or monitored. Biosignals may be electrical or non-electrical signals. Signal variations can be time variant or spatially variant. Examples of biosignals include, but are not limited to, electroencephalogram (EEG), electrocardiogram (ECG), electromyogram (EMG), mechanomyogram (MMG), electrooculography (EOG), galvanic skin response (GSR) and magnetoencephalogram (MEG) signals.

Bioelectrical measurements include electrocardiograms (ECG), electrogastrograms (EGG), electroencephalograms (EEG), and electromyography (EMG). The bioimpedance measurements include plethysmography (e.g., for respiration), body composition (e.g., hydration, fat, etc.), and electroimpedance tomography (EIT). Biomagnetic measurements include magnetoneurograms (MNG), magnetoencephalography (MEG), magnetogastrogram (MGG), magnetocardiogram (MCG). Biochemical measurements include glucose/lactose measurements which may be performed using chemical analysis of the wearer 600's sweat. Biomechanical measurements include blood pressure. Bioacoustics measurements include phonocardiograms (PCG). Biooptical measurements include orthopantomogram (OPG). Biothermal measurements include skin temperature and core body temperature measurements.

The sensor assembly 104 while shown on the external surface of the garment 1 in FIG. 1 is typically provided on an internal surface of the garment 1 such that the sensing electrodes 106, 108 may be proximate to or in contact with the skin surface of the user wearing the garment 1. The electronic device 102 may be provided on an external or internal surface of the garment 1. Openings in the garment 1 may enable the electronic device 102 to electrically conductively connect to the electronic device interface 104. In other examples, the electronic device interface 114 may be located on an external surface of the garment 1 and the sensing electrodes 106, 108 may be located on an internal surface of the garment 1.

The electronic device 102 is configured to be removably attached to the sensor assembly 104 at the electronic device interface 114.

In this exemplary embodiment, the first and second sensing electrodes 106, 108 are both blob electrodes and include a conducting portion in the form of tracking 110, 112 to couple the sensing electrodes 106, 108 to the electronic device interface 114. The first and second sensing electrodes 106, 108 are not required to have blob shapes and other arrangements such as annular or rectangular shaped electrodes are within the scope of the present disclosure. It will be appreciated that the skilled person will select a shape and size of electrode for the particular type of biosignal to be measured.

In the embodiment described herein, the tracking 110, 112 has a wavy configuration. The wavy configuration of the tracking 110, 112 accommodates flexing, stretching and movement of the material without degrading them. The wavy configuration is not required and is just one example.

The tracking 110, 112 includes respective terminating portions 110a, 112a having a configuration that defines the electronic device interface 114 as will be described in further detail below.

The sensing electrodes 106, 108, the respective elongate tracking 110, 112 and the electronic device interface 114, are formed of conductive transfers or conductive threads.

Figure 11:
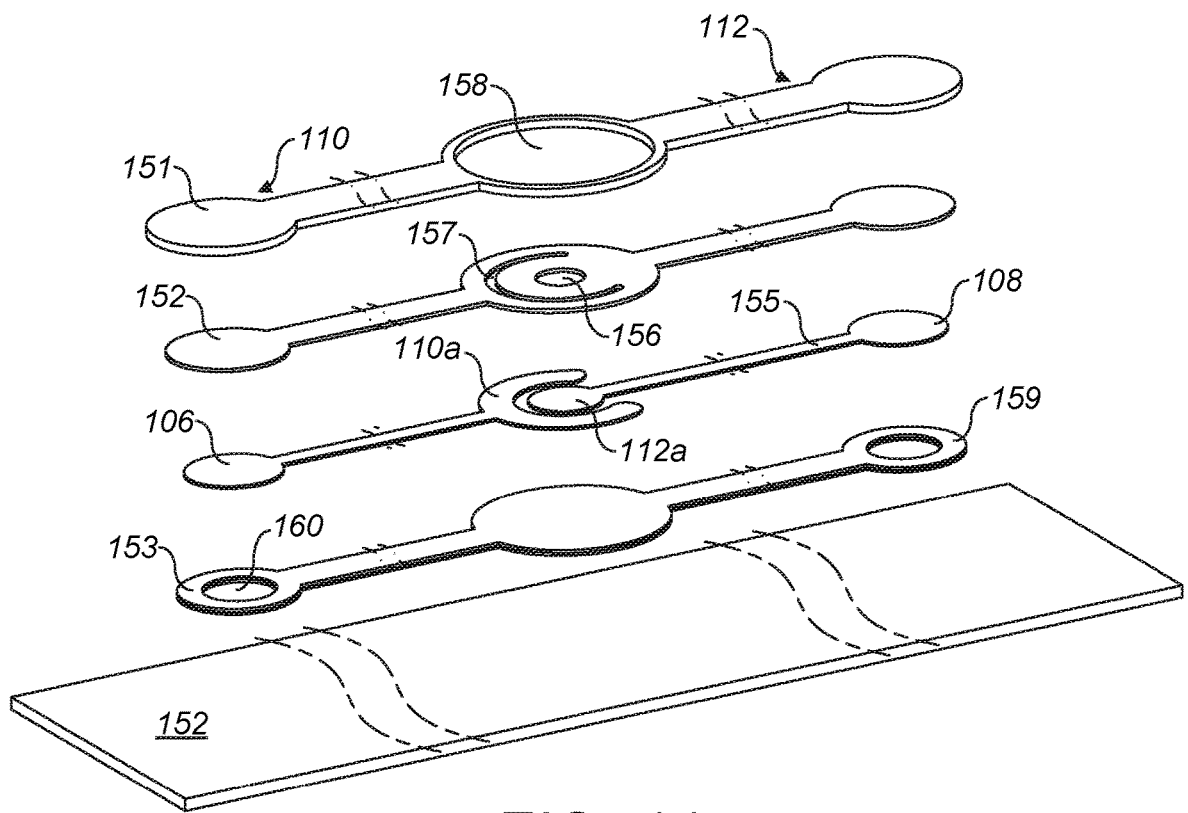
FIG. 11 is an exploded view schematically illustrating a conductive transfer of the sensor assembly.
Figure 12:
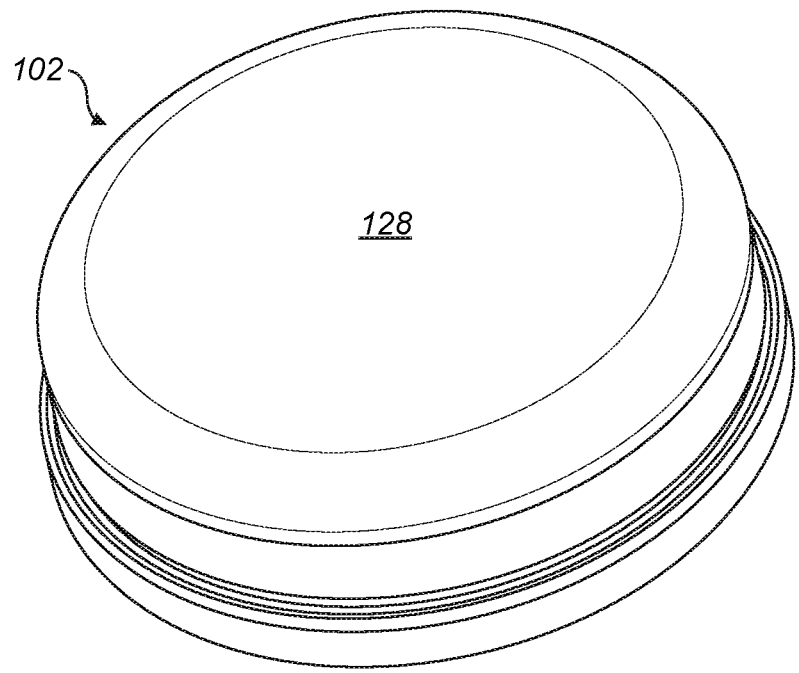
FIG. 12 is a perspective view of an electronic device for use with an alternative conductive transfer structure.

FIG. 11 is an exploded view schematically illustrating a conductive transfer forming the sensing electrodes 106, 108, tracking 110, 112 and terminating portions 110a, 112b.

The conductive transfer comprises an electrically conductive layer 155, comprising mixture of silver ink (or other conductive ink), sandwiched between an inwardly-facing insulating layer 153 and an outwardly-facing insulating layer 152.

Each sensing electrode 106, 108, with respective elongate tracking 110, 112 and terminating portion 110a, 112a comprises the conductive layer 155.

Where conductive transfers are used to form the sensing electrodes 106, 108, tracking 110, 112 and electronic device interface 114 the inwardly-facing insulating layer 153 is arranged such that, when the garment 1 is in use, the inwardly-facing insulating layer 153 faces the skin of the wearer.

Areas of the conductive layer 155 can be exposed by forming respective openings in the inwardly facing insulating layer 153 and outwardly facing insulating layer 152. In particular, the inwardly-facing layer 153 includes openings 159, 160 which expose areas of the conductive layer 155 to form the sensing electrodes 108, 106 and, and the outwardly-facing layer 152 has openings 156, 157 which expose areas of the conductive layer 155 which conform to the terminating portions 110a, 112a and which form the electronic device interface 114.

An adhesive layer 151 is provided on top of the outwardly facing insulating layer 152 to adhere the conductive transfer to the garment 1. The adhesive layer 151 includes a circular aperture 158 which aligns with the terminating portions 110a, 112a and the corresponding openings 157, 156 and to which the electronic device 2 will also be aligned.

Thus, the sensing electrodes 106, 108 face the skin of the wearer, whereas the electronic device interface 114 is towards the outer surface 3 of the garment 1 so that the electronic device 102 can be easily located against the electronic device interface 114. The garment 1 includes apertures 161, through which portions of contacts, 138a, 138b of the electronic device 102 can extend to engage with the terminating portions 110a, 112a. This will be described further below.

In an alternative, the electronic device 102 can be attached on the first, inner surface 2 of the garment 1.

A protective layer 154 is also provided but which is removed once the conductive transfer has been applied to the garment 1.

Conductive transfers are known to persons skilled in the art and are described in more detail in GB 2555592 B the disclosures of which are hereby incorporated by reference.

As mentioned above, the sensing electrodes 106, 108 are arranged to contact the wearer's skin when the garment 1 is being worn. In this exemplary embodiment, the sensing electrodes 106, 108 are provided on an inner surface 2 of a main part of garment 1 so that they are located against the skin at a region of the wearer's body that enables biosignals to be sensed.

The electronic device interface 114 is preferably located at an appropriate location on the garment 1 such that the electronic device 102 (when attached at the electronic device interface 114) is easily accessible by a wearer of the garment 1 for attachment and removal.

Preferably, the sensing electrodes 106, 108 are provided in the vicinity of the electronic device 102 as this helps to reduce collected signal noise as the communication distance between the electronic device 102 and the sensing electrodes 106, 108, is reduced.

As mentioned above, the electronic device 102 is removable, that is it is detachably connectable to the garment 1 and, in particular, to the electronic device interface 114 of the sensor assembly 104.

The electronic device 102 is removable and the sensor assembly 104 are configured to measure biosignals such as electrocardiography, bioelectricity and bioimpedance signals as well as other measurements of biophysical parameters as may be appropriate. Such measurements are informative in monitoring health and fitness of a wearer, particularly during exercise. The data can then be communicated to an external device for further processing analysis and display as required.

The removable electronic device 102 contains all the components required for data transmission and processing such that the wearable article only comprises the sensor assembly 104.

The electronic device 102 comprises, at least, a power source 116, a processor 118 and a communications module 120, along with electrical and electronic components 126 and associated circuitry to receive electrical signals, data and information from the sensor assembly 104 and carry out the appropriate processing as required. It will be appreciated that the communications module 120 is not required in all implementations of the present disclosure and instead the electronics module 102 as the electronics module 102 may not be required to transfer data or may transfer data over a wired interface such as a USB interface.

The electronic device 102 is appropriately programmed (which includes the device being programmable, or the program being embedded in the device) to perform the functions described herein. The communications module 120 enables information to be transmitted from the electronic device 102 for subsequent processing or analysis.

In the embodiment described herein the power source 116 is a battery 124, although the power source 116 may comprise a plurality of power sources.

The battery 124 may be a rechargeable battery. The battery 124 may be a rechargeable battery adapted to be charged wirelessly such as by inductive charging.

Alternatively, the power source 116 may comprise an energy harvesting device. The energy harvesting device may be configured to generate electric power signals in response to kinetic events such as kinetic events performed by a wearer of the wearable article. The kinetic event could include walking, running, exercising or respiration of the wearer. The energy harvesting material may comprise a piezoelectric material which generates electricity in response to mechanical deformation of the converter. The energy harvesting device may harvest energy from body heat of a wearer of the wearable article. The energy harvesting device may be a thermoelectric energy harvesting device.

In another alternative, the power source may be a super capacitor, or an energy cell.

In the embodiment described herein the communications module 120 is a mobile/cellular communicator operable to communicate the data wirelessly via one or more base stations in accordance with known protocols. The cellular communication network may be a fourth generation (4G) LTE, LTE Cat M1, LTE Cat M2, LTE Advanced (LTE-A), NB-IoT, fifth generation (5G), sixth generation (6G), and/or any other present or future developed cellular wireless network.

Alternatively, or in addition, the communications module 120 may provide wireless communication capabilities for the garment 1 and enables the garment 1 to communicate via one or more wireless communication protocols such as used for communication on: a wireless wide area network (WWAN), a wireless metro area network (WMAN), a wireless local area network (WLAN), a wireless personal area network (WPAN), Bluetooth® Low Energy, Bluetooth® Mesh, Bluetooth® 5, Thread, Zigbee®, IEEE 802.15.4, Ant, a near field communication (NFC), and a cellular communication network.

The electronic device 102 may further comprise a Universal Integrated Circuit Card (UICC) that enables the wearable article to access services provided by a mobile network operator (MNO) or virtual mobile network operator (VMNO). The UICC may include at least a read-only memory (ROM) configured to store an MNO/VMNO profile that the electronic device 102 can utilize to register and interact with an MNO/VMNO. The UICC may be in the form of a Subscriber Identity Module (SIM) card. The electronic device 102 may have a receiving section arranged to receive the SIM card. In other examples, the UICC is embedded directly into a controller of the electronic device 102. That is, the UICC may be an electronic/embedded UICC (eUICC). A eUICC is beneficial as it removes the need to store a number of MNO profiles, i.e. electronic Subscriber Identity Modules (eSIMs). Moreover, eSIMs can be remotely provisioned to electronic device 102. The electronic device 102 may comprise a secure element that represents an embedded Universal Integrated Circuit Card (eUICC).

A first communicator of the electronic device 102 may be provided for cellular communication and a separate communicator may be provided for short-range local communication over WLAN, WPAN, NFC, or Bluetooth®, WiFi® or any other electromagnetic RF communication protocol.

The electronic device 102 comprises a housing 128. The housing 128 comprises an upper, lid portion 128a and a lower, base portion 128b. The housing 128 is formed in two parts for ease of manufacture.

The housing 128 is circular in shape with a central axis, z. It will be appreciated that this is only one, preferred, example shape of housing 128. In other examples, only the base portion 128b may have a circular shape.

The base portion 128b has an internal cavity 149 and a circular internal recess 145 which defines an internal circumferential and radially extending surface 147.

The underside 136 of the base portion 128b has two apertures 140a, 140b provided therein. One of the apertures 140b is coincident with the central axis, z and the second of the apertures 140a is displaced in a radial direction from the first aperture 140a. This is just one example. Both of the apertures 140a, 140b may be displaced in the radial direction from the central axis, z.

A printed circuit board (PCB) 134 is arranged within the housing 128 and onto which the required components 126 for the electronic device 102 are mounted. These include the processor 118, and the communications module 120. In the present embodiment, the PCB 134 and battery are circular to locate within the housing 128.

The battery 124 is located underneath the PCB 134 and coupled to the components 126 to provide power thereto as is known in the art.

A circular disk-shaped magnet 132 is arranged within the housing 128 underneath the battery 124 and towards the underside 136 of the housing 128.

L-shaped contacts, 138a, 138b extend are connected to the PCB 134. An arm 142 of each of the L-shaped contacts 138a, 138b includes a V-shaped projection 144a, 144b.

An arm 142 of each contact 138a, 138b extends from the inner wall 150 of the base portion 128b, above the radially extending surface 147, towards the centre of the housing 128 and terminate towards a respective one of the apertures 140a, 140b so that the V-shaped projections 144a, 144b are located coincident with a respective one of the apertures 140a, 140b.

The L-shaped contacts 138a, 138b are able to flex from a first, resting position to a second, engaged, position in which the contacts 138a, 138b, and, in particular the V-shaped projections 144a, 144b, engage with the terminating portions 110a, 112a as will be described in further detail below.

In the present embodiment, the L-shaped contacts 138a, 138b are made from any suitable conducting material. As an example, the contacts 138a, 138b are made from spring brass sheet, that are stamped into strips and bent, and then coated in gold. This material selection is non-magnetic and has good electrical contact and the gold plating helps with anti-corrosion.

Other contact types could be used such as spring-loaded contacts or another form of leaf-spring contact.

The L-shaped contacts 138a, 138b are biased to a first position in which the V-shaped projections are located above and coincident with a respective aperture 140a, 140b

In the embodiment described herein, two L-shaped contacts 138a, 138b are provided. The contacts form a coupling mechanism that couples the biosignals from the sensor assembly 104 to the components 126 for processing thereby.

The L-shaped contacts 138a, 138b are preferably soldered to the PCB 134 in the same manner as conventional components are soldered to a PCB. This provides good mechanical strength to the connection.

Additional L-shaped contacts (with attendant apertures) can be provided where there are additional electrodes.

Figure 9:
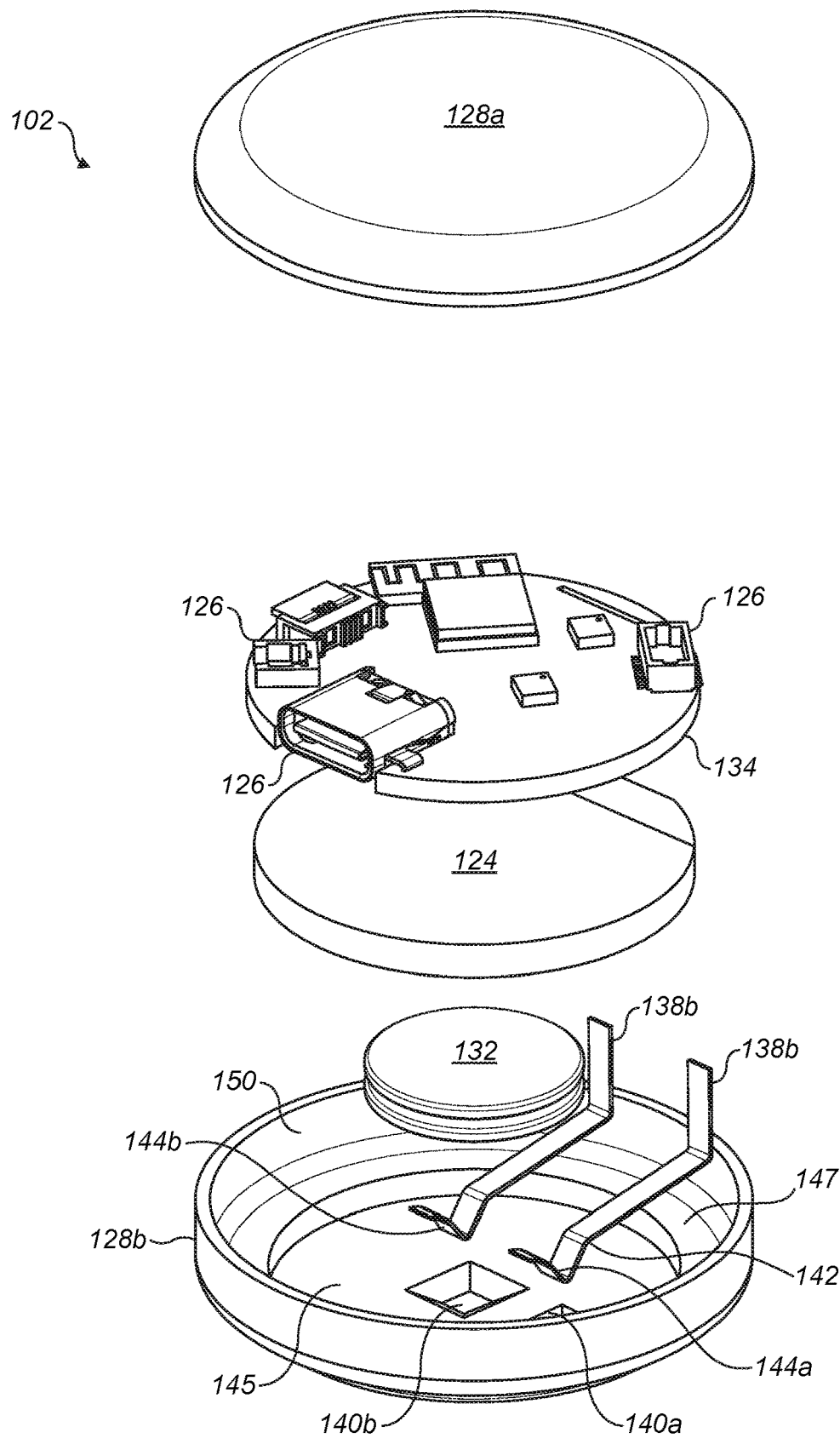
FIG. 9 is an exploded view of the electronic device of FIGS. 6 and 7.
Figure 10:
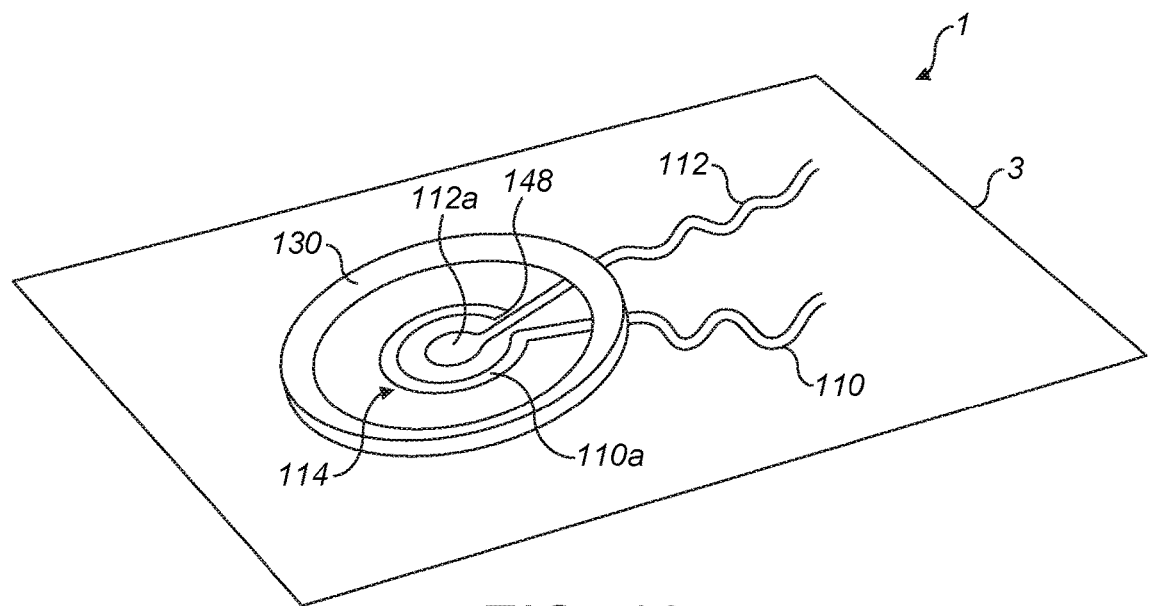
FIG. 10 corresponds to FIG. 8, but without the contacts.

When the electronic device 102 is assembled, the centre of the housing 128, the magnet 132, battery 124, and PCB 134 are all aligned with the central axis, z, as illustrated schematically in FIG. 9.

In this way, the housing 128 can be rotated around the central axis z whilst maintaining the relative alignment of the magnet 132, battery 124 and PCB 134. The provision of the circular internal recess 145, the radially extending surface 147 and the internal wall 150 configure to maintain the alignment of the L-shaped contacts 138a, 138b in relation to the apertures 140a, 140b.

The respective first and second terminating portions 110a, 112a of the tracking 110, 112 have a configuration that defines the electronic device interface 114.

Figure 2:
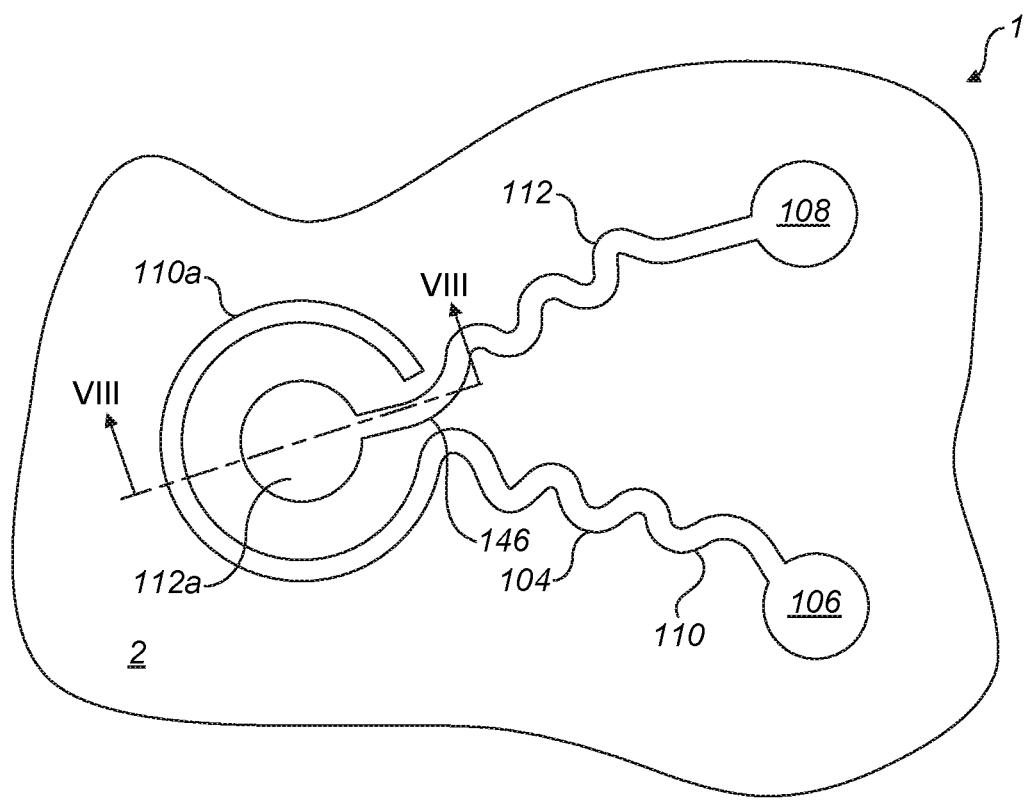
FIG. 2 is a schematic representation of a sensor assembly for incorporation in the wearable article of FIG. 2.
Figure 3:
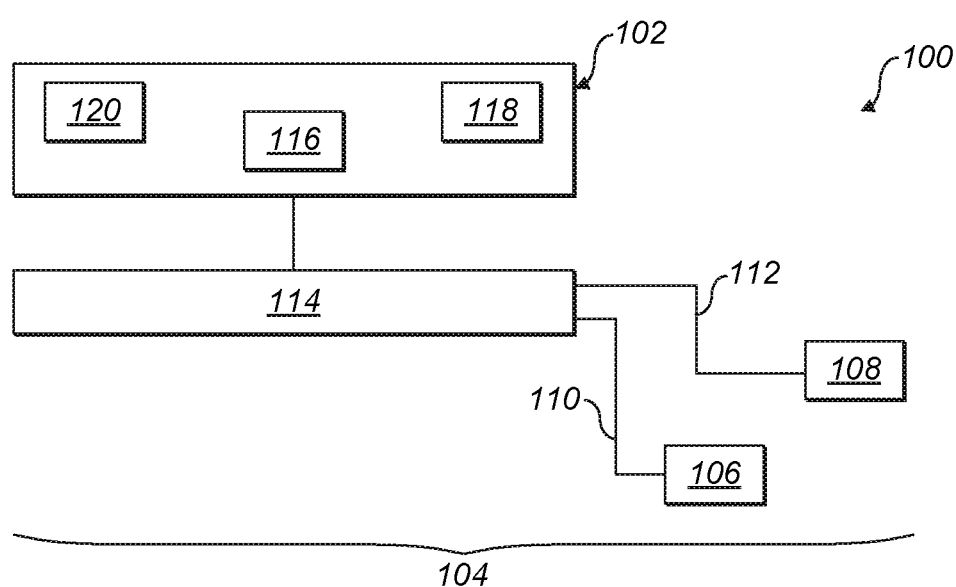
FIG. 3 is a schematic representation of the components of a measuring apparatus for the wearable article of FIG. 1.
Figure 4:
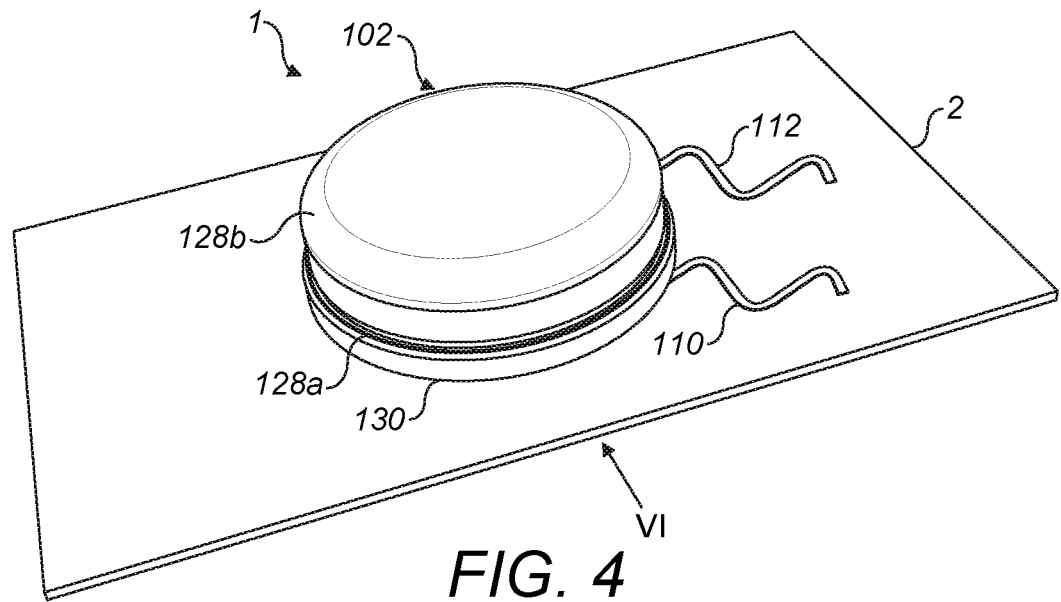
FIG. 4 is a first perspective illustration of the electronic device of FIG. 3 attached to the wearable article.
Figure 5:
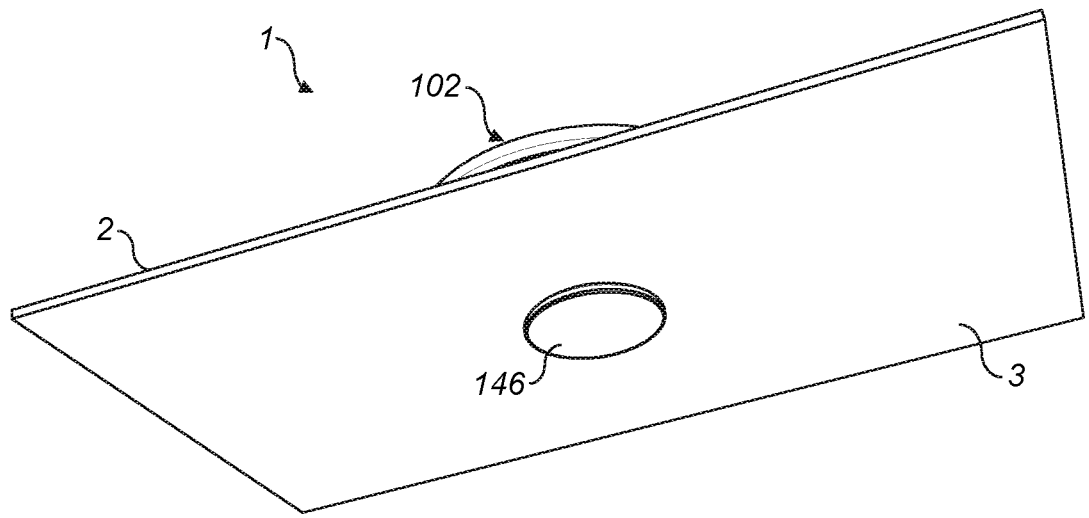
FIG. 5 is a second perspective illustration of the electronic device of FIG. 3 attached to the wearable article.
Figure 6:
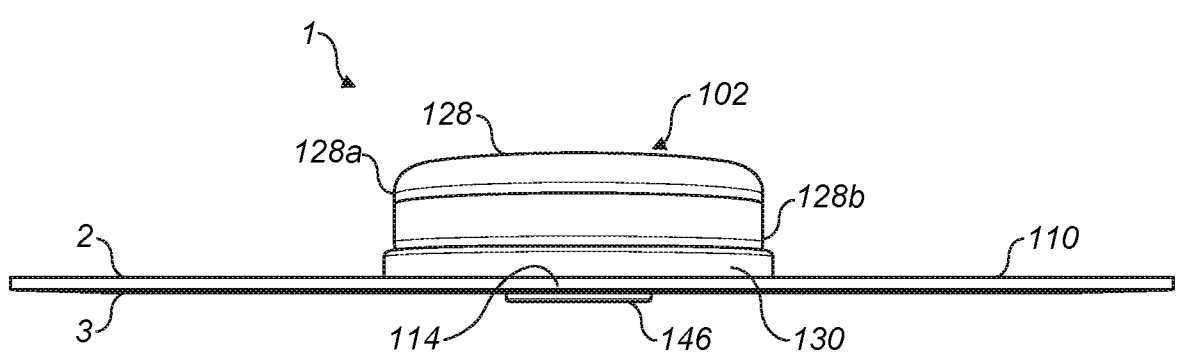
FIG. 6 is a side view of the electronic device of FIG. 4 in the direction of arrow VI of FIG. 4.

In the embodiment described herein, the first terminating portion 110a describes an arc and defines an aperture or gap 148 'through which a section of the second tracking 112 can extend. The second terminating portion 112a is a blob or roundel which is arranged substantially concentrically with the arc of the terminating portion 110a of the first tracking 110. This is illustrated schematically in FIG. 2.

The concentric roundel and arc of the tracking define the electronic device interface 114.

The electronic device 102 is arranged to be attached to the electronic device interface 114 in such a way that the V-shaped projections 144a, 144b can engage a respective one of the terminating portions 110a, 112a through the apertures 140a, 140b, when flexed to a second engaged position.

A circular disk-shaped magnet 146 is provided on the second surface 3 of the garment 1 at a location coincident with the electronic device interface 114.

When the electronic device 102 is located against the electronic device interface 114, the two magnets 146, 132 are attracted and so hold the electronic device 102 to the garment 1 along the Z axis, and to a lesser extent the X and Y axis, due to the magnetic field. Thus, the two magnets 146, 132 form an attachment mechanism for the sensor assembly 104.

The relative orientations of the terminating portions 110a, 112a, and the apertures 140a, 140b are configured such that the apertures 140a, 140b are coincident with a respective terminating portion 110a, 112a when the electronic device 102 is located against the electronic device interface 114.

The L-shaped contacts 138a, 138b have a relatively low spring force and the magnets 146, 132 only need to be strong enough to hold the weight of the electronic device 102.

Figure 7:
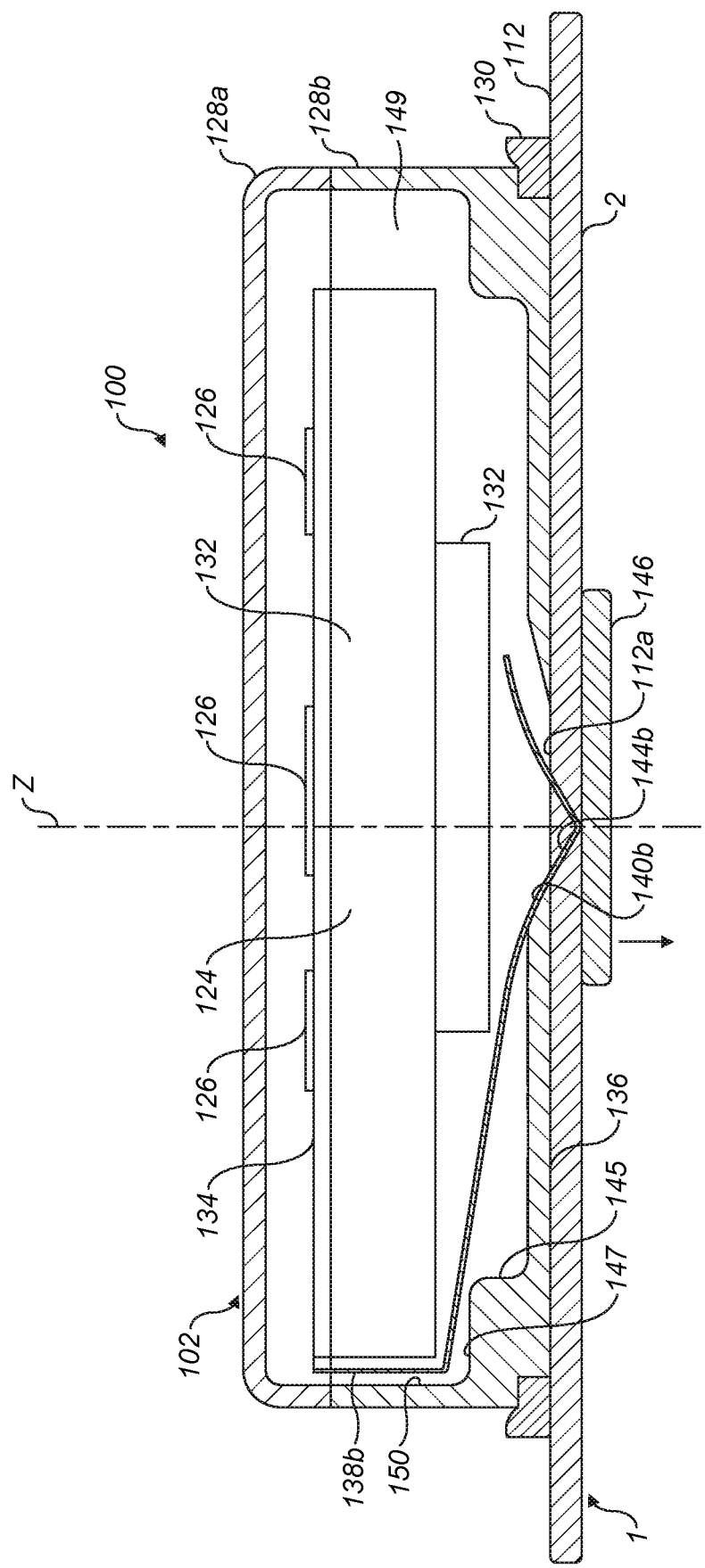
FIG. 7 is a cross-sectional view across the diameter of the electronic device of FIG. 4, along the line VIII-VIII shown in FIG. 2.

The forces exerted by the magnet 132, when the electronic device 102 is attached to the electronic device interface 104, acts on the L-shaped contacts 138a, 138b to cause the L-shaped contacts 138a, 138b to flex, in the direction of the arrow in FIG. 7, to the second position in which the V-shaped projections 144a, 144b move into the respective aperture 140a, 140b and into engagement with the respective terminating portion 110a, 112a.

Figure 8:
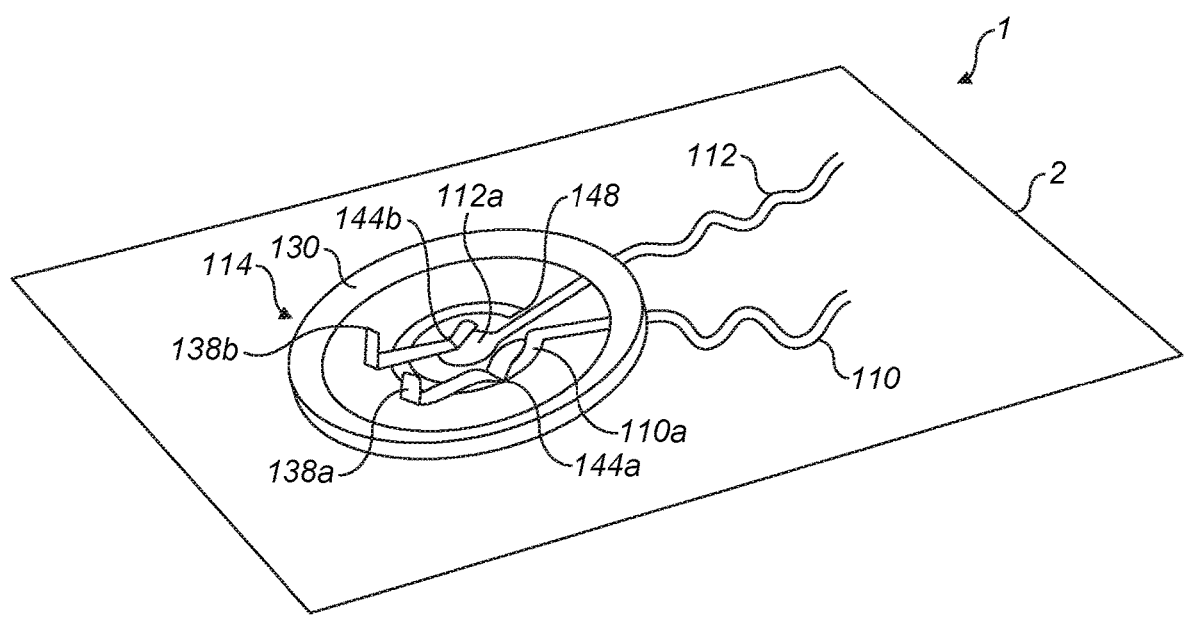
FIG. 8 is a perspective view of the electronic device interface of the sensor assembly illustrating how contacts of the electronic device engage with the terminating portions of the sensor assembly.

FIG. 8 shows how the contacts 138a, 138b engage the terminating portions 110a, 112a.

The concentric orientation of the terminating portions 110a, 112a and the relative orientation of the apertures 140a, 140b, where one aperture 140b is coincident with the central axis z, and the other aperture 140a is located on a diameter i.e. radially displaced from the first aperture 140b, then the electronic device 102 can be rotated around the central axis z and the L-shaped contacts 138a, 138b, and in particular the V-shaped projections 114a, 144b will continue to follow the tracking 110, 112 and, in particular the terminating portions 110a, 112a of the tracking 110, 112.

The circular configuration of the internal cavity 145 helps to keep the battery 124, magnet 132 and PCB 134 aligned with the central axis, z.

In order to limit movement of the electronic device 102 in the X and Y axes, the electronic device interface 114 includes a locator 130 provided to the upper first surface 2 so as to circumscribe the electronic device interface 114. The locator 130 is a circular ring and of a dimension that encloses the first and second terminating portions 110a, 112a and receives the base portion 128a of the housing 128.

The locator 130 is contoured to match the profile of the base portion 128a of the housing 128.

The locator 130 is made from compression foam and dimensioned so that, when the housing 128 is placed within the locator 130 there is an interference fit around the circumference of the base portion 128b which provides friction to the rotation of the unit, reducing contact abrasion and prolonging the lifetime of the conductive transfers.

As the locator 130 is resilient, the electronic device interface 114 is flexible. This design avoids bulky plastics in the garment. The locator 130 also provides a 'sealing' ring, limiting water ingress. This garment 1 is washable, and the electronic device 102 is wipe cleanable.

The locator 130 could include a keying mechanism such as a lip (not shown) extending radially inward of the locator 130 and the housing could include a radially inwardly extending recess (not shown) configured to engage with lip to enhance retention and location of the electronic device 102 on the garment 1. Conversely, the lip could be provided on the housing.

The keying mechanism may be provided on the garment 1 rather than on the locator 130.

In use, therefore, the electronic device 102 can be manually placed within the locator 130 so that the L-shaped contacts 138a, 138b engage with the respective terminating portions 110a, 112a of the electronic device interface 114. The magnets 146, 132 are attracted together and keep the electronic device 102 in place thus allowing data relating to the sensed biosignals to be coupled to the electronic device 102 and processed accordingly. The locator 130 and magnets 146, 132 allow for simple connection which can easily be achieved manually without significant attention from the wearer and easily with one hand.

In an alternative, the housing 128 can include three apertures in the base portion 128b. One of these apertures will be located centrally of the base portion 128b coincident with the vertical, z, axis of the housing 128. Second and third apertures are provided equidistantly of the central aperture 140b and on the diameter. One contact is configured to cooperate with the centrally located aperture whilst second and third contacts are configured to cooperate with respective second and third apertures. The second and third contacts are both coupled to each other. In this way, at least one or other of the second and third contacts is always in contact with the outer terminating portion 110a, even if the other of the second or third contacts moves out of contact with the terminating portion 110a e.g. at the gap 148.

As an alternative configuration for the outer terminating portion 110a, rather than being a continuous track, the outer terminating portion can have a piecewise configuration with gaps between each section (for example, if there are more than two sensing electrodes). In this embodiment, the use of three or more contacts as described above can be utilised.

In a further alternative, when more than two sensing electrodes is used in the sensor assembly 104, the terminating portions of two of which can be configured as as concentric circular tracks around an inner electrode that can be a blob electrode or another circular track. In this case, tracking will be provided for all the electrodes will terminate in the electronic device interface 114 and corresponding contacts will be provided in the electronic device 102 to engage with the respective tracking as described above. The circular electrodes can be continuous tracks or have a piecewise configuration.

An alternative conductive transfer structure is illustrated in FIGS. 12 to 15.

In this alternative embodiment, the first terminating portion 110a of the first tracking 110 has a circular configuration and the second terminating portion 112a of the second tracking 112 is a blob, with two terminating portions 110a, 112a being concentrically arranged.

As with previous embodiments, first and second tracking 110, 112 and the respective terminating portions 110a, 112a are formed as electrically conducting layers of a conductive transfer. An insulating layer (not shown) is provided between the electrically conducting layers that form first and second tracking 110, 112 and terminating portions 110a, 112b.

In the embodiment described herein the electronic device 102 is as described above and is illustrated in FIGS. 12 and 13. The electronic device comprises a housing 128.

Figure 13:
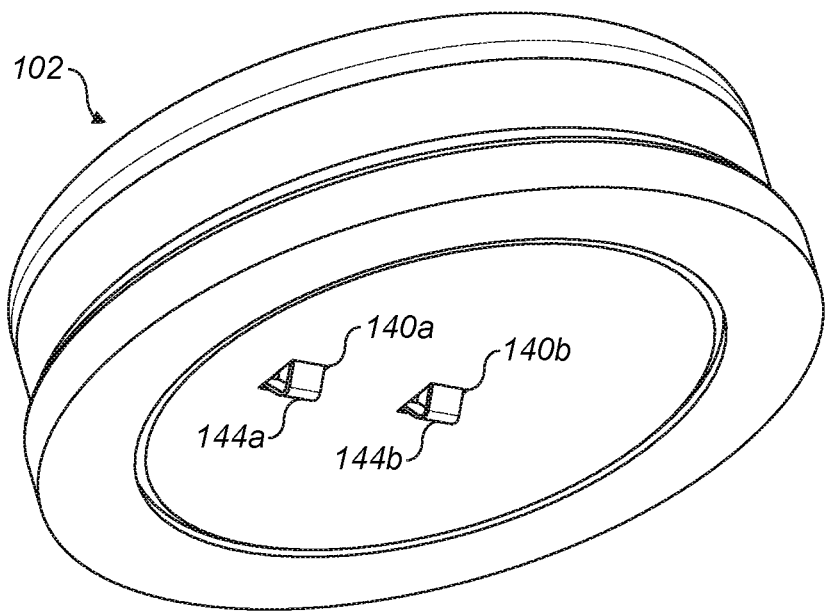
FIG. 13 shows the underside of the electronic device of FIG. 12.

FIG. 13 shows the underside of the housing 128.

Figure 14:
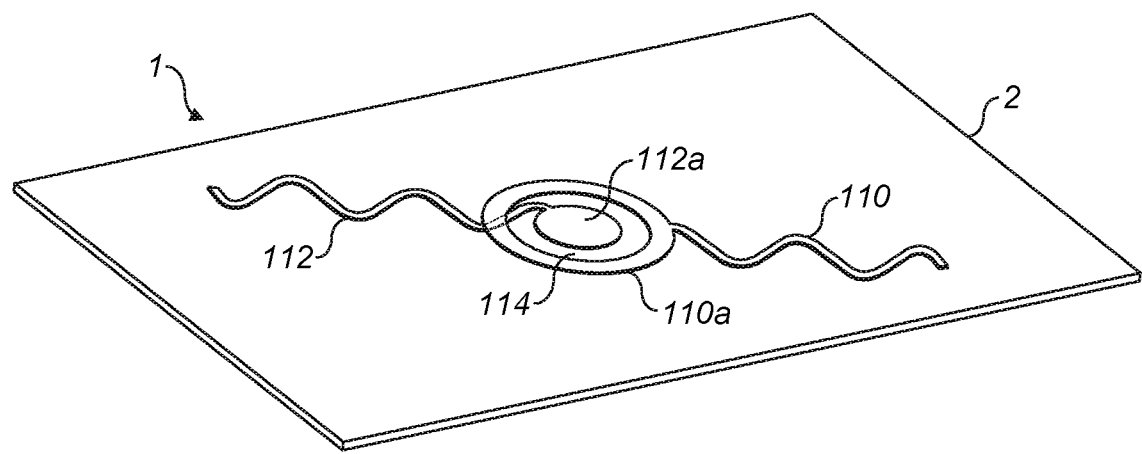
FIG. 14 illustrates an alternative conductive transfer structure.
Figure 15:
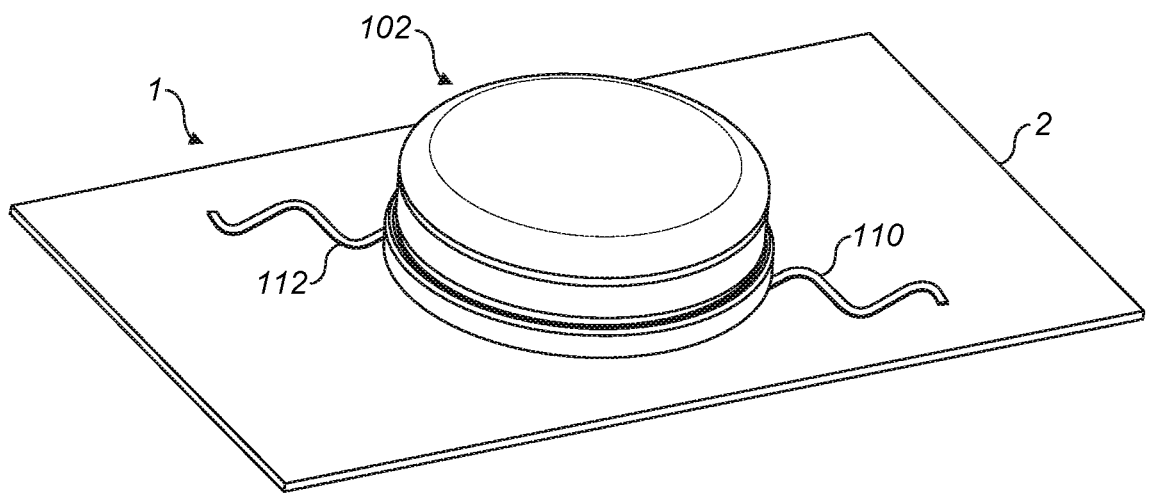
FIG. 15 illustrates the housing of FIGS. 12 and 13 attached to a garment incorporating the alternative conductive transfer structure of FIG. 14.

FIG. 14 illustrates the electronic device 128 attached to the garment 1.

Other housing shapes, such as rectangular or other polygonal shapes, can be used. Such housing shapes are within the scope of the present disclosure. It will be appreciated that the skilled person will select a shape and size of housing for the particular type of application, components and/or garment.

When the electronic device 102 needs removing, for example, to enable the garment to be washed, then this can also be done manually and simply and easily without undue attention of the wearer.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive.

Throughout this specification, the term "comprising" or "comprises" means including the component(s) specified but not to the exclusion of the presence of others.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

For example, the terminating portions of the tracking can be concentric circles or other configurations. More than two sensing electrodes can be used with appropriate terminals and electronic device interface configurations.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. An electronic device for a wearable article, the electronic device being configured to receive biosignals from a sensor assembly provided on the wearable article and including one or more sensing electrodes, the electronic device comprising:
- a housing having a base and a magnet, said housing arranged to house components configured to receive and process the received biosignals; and
- a signal coupling mechanism configured, when the electronic device is attached to the wearable article at an electronic device interface of the sensor assembly, to couple the biosignals to the components from the sensor assembly,
- wherein the signal coupling mechanism comprises at least one contact coupled to the components and configured to engage with the sensor assembly at a terminal of a respective sensing electrode, and
- wherein the at least one contact is an electrical contact positioned in the housing in a first position that flexes into a second position outside of the housing due to the forces exerted by the magnet on the at least one contact; and the at least one contact engages with the terminal of the respective sensing electrode when the electronic device is attached to the wearable article;
wherein the housing includes at least one aperture in the base through which a portion of the at least one contact extends to engage with the terminal of the respective sensing electrode when in the second position.

2. The electronic device according to claim 1, wherein the components are mounted on a circuit board located within the housing and the at least one contact is connected to the components on the circuit board.

3. The electronic device according to claim 1, wherein the portion of the at least one contact is a projection which engages the terminal of the respective sensing electrode.

4. The electronic device according to claim 3, wherein the at least one contact is L-shaped and includes an arm extending inwardly of the housing, and the projection is a V-shaped projection from the arm.

5. The electronic device according to claim 1, wherein the housing is a circular housing with a central axis around which the circular housing can rotate.

6. The electronic device according to claim 5, wherein the circular housing includes an outer wall, and a circumferential surface extending radially inwards from the outer wall and defining an internal circular recess, the circumferential surface being configured to maintain alignment of the at least one contact within the circular housing.

7. The electronic device according to claim 6, wherein the at least one aperture is located on a diameter of the circular housing.

8. The electronic device according to claim 7, wherein the at least one aperture is located coincidentally with the central axis.

9. The electronic device according to claim 5, wherein the circular housing includes two or more apertures in the base, each of the apertures being located on an internal diameter of the circular housing, and the electronic device has two or more electrodes, and wherein a portion of the at least one contact extends through a respective one of the two or more apertures to engage with the terminal of the respective sensing electrode.

10. The electronic device according to claim 9, wherein one of the two or more apertures is located coincidentally with the central axis, and another of the two or more apertures is displaced radially from the one of the two or more apertures.

11. The electronic device according to claim 9, wherein the circular housing includes three apertures in the base and each of the three apertures being located on an internal diameter of the circular housing, a first of the three apertures being located centrally on the base and coincident with the central axis, and the second and the third apertures being located equidistantly of the first aperture and on the diameter of the circular housing, and the electronic device has three contacts, wherein a portion of each of the three contacts extends through a respective one of the three apertures to engage with the terminal of the respective sensing electrode, wherein a first of the three contacts is configured to cooperate with the first of the three apertures whilst the second and third contacts are configured to cooperate with the respective second and third apertures, and wherein the second and third contacts are coupled to each other.

12. The electronic device according to claim 1, wherein the components are mounted on a circuit board located within the housing and the at least one contact is connected to the components on the circuit board.

13. The electronic device according to claim 12, wherein the portion of the at least one contact is a projection which engages the terminal of the respective sensing electrode.

14. The electronic device according to claim 13, wherein the at least one contact is L-shaped and includes an arm extending inwardly of the housing, and the projection is a V-shaped projection from the arm.

15. The electronic device according to claim 1, wherein the housing is a circular housing with a central axis around which the circular housing can rotate, wherein the at least one aperture is located on a diameter of the circular housing.

16. The electronic device according to claim 15, wherein the at least one aperture is located coincidentally with the central axis.

17. The electronic device according to claim 15, wherein the circular housing includes two or more apertures in the base, each of the two or more apertures being located on an internal diameter of the circular housing, and the electronic device has two or more electrodes, and wherein a portion of the at least one contact extends through a respective one of the two or more apertures to engage with a terminal of the respective sensing electrode.

18. The electronic device according to claim 17, wherein one of the two or more apertures is located coincidentally with the central axis, and another of the two or more apertures is displaced radially from the one of the two or more apertures.

19. The electronic device according to claim 18, wherein the circular housing includes three apertures in the base, each of the three apertures being located on an internal diameter of the circular housing, a first of the three apertures being located centrally on the base and coincident with the central axis of the circular housing, and the second and third apertures being located equidistantly of the first of the three apertures and on the diameter of the circular housing, and the electronic device has three contacts, wherein a portion of each of the three contacts extends through a respective one of the three apertures to engage with the terminal of the respective sensing electrode, wherein a first of the three contacts is configured to cooperate with the first of the three apertures whilst the second and third contacts are configured to cooperate with respective second and third apertures, and wherein the second and third contacts are coupled to each other.

20. A biosignal measuring system comprising the wearable article and the electronic device according to claim 1, wherein the sensor assembly comprises:

the one or more sensing electrodes for sensing the biosignals; and the electronic device interface coupled to the at least one sensing electrodes and configured to couple the sensed biosignals to the electronic device, wherein each of the at least one sensing electrodes includes the terminal configured to engage with the signal coupling mechanism of the electronic device when the electronic device is attached to the sensor assembly at the electronic device interface.

21. A biosignal measuring system comprising the wearable article and the electronic device according to claim 12, wherein the sensor assembly comprises:

the one or more sensing electrodes for sensing the biosignals; and the electronic device interface coupled to the at least one sensing electrodes and configured to couple the sensed biosignals to the electronic device, wherein each of the at least one sensing electrodes includes the terminal configured to engage with the signal coupling mechanism of the electronic device when the electronic device is attached to the sensor assembly at the electronic device interface.

22. A biosignal measuring system comprising the wearable article and the electronic device according to claim 15, wherein the sensor assembly comprises:

the one or more sensing electrodes for sensing the biosignals; and the electronic device interface coupled to the at least one sensing electrodes and configured to couple the sensed biosignals to the electronic device, wherein each of the at least one sensing electrodes includes the terminal configured to engage with the signal coupling mechanism of the electronic device when the electronic device is attached to the sensor assembly at the electronic device interface.

* * * * *